United States Patent [19]

Jowett

[11] Patent Number: 5,063,189

[45] Date of Patent: Nov. 5, 1991

[54] RANEY CATALYST COMPOSITION

[76] Inventor: Peter Jowett, Tame Street, Stalybridge, Cheshire, SK15 1QW, England

[21] Appl. No.: 500,604

[22] Filed: Mar. 29, 1990

[30] Foreign Application Priority Data

Jul. 31, 1987 [GB] United Kingdom ................ 8718231

[51] Int. Cl.$^5$ ............................................. B01J 25/00
[52] U.S. Cl. ................................... 502/150; 502/173; 502/301
[58] Field of Search ........................ 502/150, 173, 301

[56] References Cited

FOREIGN PATENT DOCUMENTS 1555015 1/1969 France .
633165 6/1947 United Kingdom .
791658 4/1956 United Kingdom .
1475689 6/1973 United Kingdom .
1563690 4/1978 United Kingdom .
2052296 5/1980 United Kingdom .
2121697 6/1982 United Kingdom .

OTHER PUBLICATIONS

Ciapetta et al, C.A. vol. 72(1970)16100e.

Primary Examiner—Patrick P. Garvin
Assistant Examiner—Brent M. Peebles
Attorney, Agent, or Firm—Nixon & Vanderhye

[57] ABSTRACT

A Raney catalyst composition comprises Raney metal coated with fatty monoglyceride.

16 Claims, No Drawings

RANEY CATALYST COMPOSITION

The present invention relates to a Raney metal catalyst composition which is useful for hydrogenation reactions. The invention relates particularly, but not exclusively, to a Raney nickel catalyst composition.

The process of hydrogenation, i.e., the reaction of hydrogen gas with organic substances having unsaturation in the molecule is well known. Hydrogenation is extremely important for industrial chemicals and for oils and fats hardening, both in the field of industrial chemicals and in the fields of food stuffs. A catalyst is frequently necessary for the hydrogenation to take place at a reasonable rate and this can take the form of palladium, platinum or nickel.

The usual catalyst for hydrogenation is an activated form of nickel. There are three main types of activated nickel catalyst, namely "Wet-reduced" catalyst manufactured from a decomposable salt such a nickel formate, "Dry-reduced" nickel catalyst on a diatomaceous earth, and Raney nickel catalyst.

Because "Wet-reduced" nickel catalyst produces extremely fine particles of nickel, almost of colloidal dimensions, such a catalyst gives difficulties in filtration, after hydrogenation, and its use has tended to be replaced over the last number of years by "Dry-reduced" catalyst. "Dry-reduced" catalyst is prepared from a nickel salt in an insoluble form such as nickel hydroxide, nickel carbonate, nickel bi-carbonate, and suspended on a diatomaceous earth, filtered, dried and reduced in a stream of hydrogen to form particles of diatomaceous earth on which are attached small particles of activated nickel. Such catalyst is widely used for edible oils and fats hydrogenation, since it is comparatively easy to filter and has good activity.

"Dry-reduced" nickel catalyst does however suffer from several disadvantages:

1. The nickel content is comparatively low, the bulk of the catalyst supplied being an inert form of diatomaceous earth, filter aid or Kieselguhr. Consequently when the catalyst is filtered from the hydrogenated material such as an edible oil or fat which has been partially or completely hydrogenated, the filter cake produced has a relatively low nickel content. The low nickel content renders the cake of no or low value, as a secondary form of nickel.
2. The process for manufacturing dry reduced catalyst is elaborate and expensive.

Raney nickel catalyst, or activated "sponge" nickel catalyst, is manufactured from an alloy of nickel and aluminium which is digested by a caustic alkali solution to leave the activated nickel form suspended under water.

Raney nickel catalyst readily overcomes the disadvantages mentioned above for 'Dry Reduced' catalyst since the Raney catalyst does not need to have any inert diatomaceous earth, filter aid or Kieselguhr support: it can be produced in particle sizes which are easy to filter and is much more economical to produce. However, Raney catalyst has not been much used for hydrogenation of oils and fats in the manufacture of fatty food stuffs such as shortenings, margarines, cooking fats, etc., owing to certain disadvantages:

1. It is suspended under water which makes it difficult to admix with an oil for hydrogenation.
2. The Raney catalyst is produced, supplied and suspended under water and any accidental spillages result in the water evaporating, leaving the Raney catalyst which in the dry state is pyrophoric, and igniting any combustible material next to it, rendering it unsafe to handle, distribute and use for this application.

Numerous attempts have been made to overcome these disadvantages of Raney nickel as follows:

(a) Use of solvent such as alcohol to replace the water with Raney nickel catalyst renders it more easily dispersible in oil but any accidental spillages which may occur render the product even more hazardous than under water.

(b) For industrial applications, suspending Raney nickel catalyst under a fatty amine overcomes these disadvantages and is suitable for some industrial applications (see GB-A-1475689 and U.S. Pat. No. 4,166,805.

However, the use of fatty amine could not be considered for food stuff applications:

(i) The fatty amine is not an edible substance
(ii) Fatty amines are strong alkalies and in contact with the skin could cause alkali burns.

GB-A-2 052 296 discloses a Raney catalyst composition in which the catalyst particles are dispersed in a solid wax, fat or organic polymer which intimately coats the catalyst thereby rendering the catalyst non-pyrophoric. The fat (when used) is a triglyceride ester of animal or vegetable origin, examples being hard tallow (hydrogenated tallow), soft tallow, hardened rape seed oil, ground nut oil or any hydrogenated oil. All of the waxes, fats and organic polymers disclosed in GB-A-2 052 296 are oleophilic and the catalyst compositions are prepared by firstly displacing water from the surface of the catalyst metal by means of a surface active agent so as to render the catalyst oleophilic for dispersion in the wax fat or organic polymer.

The catalyst compositions of GB-A-2 052 296 do however have the disadvantage that, because the coatings are oleophilic, the resultant catalyst composition (from which practically all of the water will have been displaced) cannot be satisfactorily used for the hydrogenation of aqueous based systems. For example, sorbitol is manufactured by the hydrogenation of an aqueous solution of glucose and it would not be possible to us the catalyst compositions of GB-A-2 052 296 for this reaction.

It is the object of the present invention to overcome all these disadvantages and enable a Raney catalyst to be made suitable for use with edible oil and for hydrogenation for food stuffs.

According to the present invention there is provided a catalyst composition comprising particulate Raney metal, for example Raney Nickel, coated with a fatty monoglyceride.

For convenience, reference will be made in the subsequent description to Raney nickel only, but it will be appreciated that the invention is applicable to other Raney metal catalysts, e.g., Raney cobalt.

The use of a monoglyceride has the advantage over the coated Raney nickel catalyst systems described above that the monoglycerides are surface active agents in their own right and are effective to displace water from the catalyst particles and coat them with monoglyceride, thus rendering the catalyst non-pyrophoric. Furthermore, water from the original Raney catalyst (as prepared under water) is emulsified in the monoglyceride material and this (coupled with the relatively polar nature of the monoglyceride) means that the catalyst composition can be used for the hydrogenation of aqueous based systems. An additional significant advantage is that the monoglyceride in which the acid residue has 8-24 carbon atoms (which are the preferred monoglycerides for use in the invention are edible, thus rendering the catalyst compositions suitable for hydrogenation reactions in the food stuffs, industry. For example, the composition may be used in the manufacture of sorbitol. Additionally the presence of water in the monoglyceride in reactions such as the reduction of nitriles to amines where the water has a beneficial effect in absorbing ammonia, enabling a selective hydrogenation of nitrite to primary amine to take place with minimum conversion to secondary amine.

As mentioned above, the preferred monoglycerides for use in the invention have an acid residue containing 8-24 carbon atoms. The acid residue in the monoglyceride may, for example, be that of stearic acid, oleic acid, or any fatty acids of animal or vegetable origin examples being soyabean fatty acids, tallow fatty acids, rape seed fatty acids, ground nut fatty acids, sunflower fatty acids, and palm oil fatty acids.

The Raney nickel catalyst is suspended under the monoglyceride product so that the catalyst particles are coated with, and protected by, the monoglyceride product in which water absorbed and/or dispersed. The monoglyceride renders the catalyst non-pyrophoric. The catalyst can be used safely for hydrogenation of oils and fats intended for food stuffs. Monoglycerides in such fats and oils assist the dispersion of the catalyst in the oils and fats to be hydrogenated.

The catalyst composition may contain water soluble substances such as glycerine, sugar solutions and glucose solutions, and may contain other oils and fats which may or may not be partially or completely hydrogenated.

The preferred embodiment of our invention is to coat a Raney nickel catalyst which is currently suspended in water with a high melting point, fatty monoglyceride. The fatty monoglyceride may be in the molecularly distilled form with over 90% monoglyceride or in some examples may be a commercial monoglyceride with a minimum of 40% monoglyceride, the remainder being a mixture of di and tri-glycerides.

By using a monoglyceride suitable for food use, which has been fully hydrogenated, such as from fully hardened soyabean oil or from fully hardened tallow, the Raney nickel catalyst suspended in this material can be prepared in a hard, solid form which is suitable for flaking or powdering. Such fully coated Raney nickel catalyst has the following advantages:

1. The catalyst is in the form which is readily filterable in conventional filtration equipment.
2. The filter cake obtained from the use of Raney catalyst has a high nickel content and is therefore of considerable value as a source of secondary nickel.
3. Many other metals such as molybdenum or cobalt can be introduced into the catalyst by smelting the nickel, aluminium and the auxiliary metal together, enabling particularly active forms of a Raney nickel hydrogenation catalyst to be produced.
4. A Raney nickel catalyst, still retaining some water, coated and suspended in a monoglyceride fatty material is readily dispersed in the material to be hydrogenated since the monoglyceride acts as a wetting agent between the catalyst and the material to be hydrogenated.
5. The catalyst is simple to produce, to those skilled in the art, with conventional equipment. In further embodiments of the invention, Raney catalyst suspended under water is first admixed with water soluble substances such as sugar solutions, glucose syrups or glycerine. If required in a further embodiment of the invention, the catalyst can be admixed with filter aid, decolorising charcoal or other aids to processing.

In an advantageous development of the invention, the Raney catalyst suspended under water may initially be "washed" with a dilute emulsion (preferably a homogenised dispersion) of a monoglyceride in water. The emulsion may comprise 10% to 30%, preferably 15% to 25%, most preferably about 25%, by weight of fatty material, although not all of this fatty material need be the monoglyceride. Thus, for example, the catalyst may be washed with a dispersion containing 20% by weight of the aforementioned commercial monoglyceride containing a minimum of 40% monoglyceride. This washing (which would generally be the final washing stage in the production of a Raney catalyst by digestion of a metal/aluminum alloy using a caustic alkali causes a coating of monoglyceride to be formed on the Raney metal which is otherwise under the dispersion of the monoglyceride. This coating of the monoglyceride to be formed on the catalyst particles thus making them more oleophilic thus facilitating further addition of monoglyceride in a final stage of manufacture. Furthermore, spillage of the catlyst in the monoglyceride dispersion results in formation of additional monoglyceride coating around the catalyst particles as the water evaporates, so that the catalyst is non-pyrophoric.

EXAMPLE 1

50 kilos of Raney nickel catalyst, suspended under water was added to a mixer which can be z-bladed, planetary, or similar and to this was added 50 kilos of a 90% minimum, molecularly distilled, monoglyceride obtained from fully hydrogenated soya bean oil sold under the trade name of "Hymono 8803", the whole contents being maintained at 80° C.

After a few minutes mixing, a uniform mass in which all of the water from the Raney catalyst was emulsified was obtained and this was passed on to a flaking band, flaked and introduced into suitable containers.

EXAMPLE 2

Process carried out identical to Example 1, the product after mixing was cast into blocks, and allowed to set for twenty-four hours. At the end of this time the product was powdered in conventional equipment and introduced into suitable containers.

EXAMPLE 3

50 kilos of Raney nickel suspended under water was introduced into a special mixing device as in Example 1 and to this was added 20 kilos of BP glycerine. The amounts was mixed together and to this maintained at 80° C. was added 30 kilos of monoglyceride, Hymono 8803. A smooth mixture was obtained which was introduced into small 10 kilo pails as a paste.

EXAMPLE 4

Example 3 was repeated except that 20 kilos of a glucose syrup with low dextrose equivalent (as offered by CPC., U.K) were used instead of glycerine. To the mixture was added 30 kilos, at 80° C. of monoglyceride Admul MG. 4203 (in which the acid residue is derived from fully hydrogenated palm oil). When a smooth mixture was obtained the product was introduced into 10 kilo pails as a paste.

EXAMPLE 5

50 kilos of Raney nickel was introduced into a mixer in a similar manner to Example 1, and after this was added 25 kilos of Hymono 8803 monoglyceride emulsifier. When a smooth consistency was obtained a further 25 kilos of fully hydrogenated soyabean oil was introduced and mixed with the contents of the mixer. When a uniform mixture was obtained the product was flaked or powdered in a similar way to previous examples.

EXAMPLE 6

A washing liquid for a Raney catalyst composition was prepared by dispersing 10% by weight of Admul MG 4203 in water at 80° C. with agitation and then homogenisation in a homogenisor. The washing liquid was cooled and used for the final washing stage in the preparation of a Raney nickel catalyst obtained by digestion of a nickel/aluminium alloy using caustic alkali.

The resultant catalyst particles were under the aqueous dispersion of the monoglyceride and had a coating of the monoglyceride. The particles could subsequently easily be dispersed in further quantity of monoglyceride in the manner described in Example 1.

EXAMPLE 7

A 1 liter flask fitted with an agitation and a hydrogen inlet tube was charged with 500 ml of soyabean oil having an Iodine value of 128. The catalyst composition of Example 1 was added to give 0.1% by weight of nickel based on the weight of the soyabean oil. The soyabean oil was heated to a temperature of 140° C. and hydrogen passed through with stirring. After 1 hour, the Iodine value was reduced to 94, after 2 hours to 70, and after 3 hours to 52.

I claim:

1. A method of preparing a Raney metal catalyst composition, which method comprises the step of treating a particulate Raney metal catalyst suspended in water with a fatty monoglyceride having a fatty acid residue of 8 to 24 carbon atoms to coat said Raney metal catalyst particles with said fatty monoglyceride.

2. A method according to claim 1, wherein said treatment is carried out until a mass is formed in which said Raney metal catalyst is dispersed in said fatty monoglyceride.

3. A method according to claim 2, wherein water from said Raney metal catalyst is emulsified in said fatty monoglyceride.

4. A method according to claim 1, wherein said fatty monoglyceride is in the form of an aqueous dispersion.

5. A method according to claim 4, and further including suspending in water the Raney metal catalyst composition produced using said aqueous dispersion of fatty monoglyceride and treating said suspended composition with a fatty monoglyceride having a fatty acid residue of 8 to 24 carbon atoms to form a mass in which the Raney metal catalyst composition is dispersed in the fatty monoglyceride.

6. A method according to claim 4, wherein said aqueous dispersion comprises 10% to 30% by weight of fatty material.

7. A method as claimed in claim 4, wherein said aqueous dispersion is a homogenized dispersion.

8. A method according to claim 1, carried out under elevated temperature.

9. A method according to claim 8, wherein said temperature is about 80° C.

10. A method according to claim 1, wherein said Raney metal is Raney Nickel.

11. A method according to claim 1, wherein other water-soluble substances are present.

12. A method according to claim 1, wherein other oils or fats are present.

13. A method according to claim 1, wherein said fatty monoglyceride is in molecularly distilled form.

14. A method according to claim 1, wherein there is present a minimum of 40% monoglyceride based on the weight of the fatty composition.

15. A method according to claim 1, wherein said fatty monoglyceride is polyhydrogenated.

16. A method according to claim 1, wherein said acid residue in said fatty monoglyceride is selected from the group consisting of stearic acid, oleic acid, soyabean fatty acids, tallow fatty acids, rape seed fatty acids, ground nut fatty acids, sunflower fatty acids and palm oil fatty acids.

* * * * *